US007683161B2

(12) United States Patent
Podhorez et al.

(10) Patent No.: US 7,683,161 B2
(45) Date of Patent: Mar. 23, 2010

(54) SELECTIVE REDUCTION OF SPINOSYN FACTORS ET-J AND ET-L TO SPINETORAM

(75) Inventors: David E. Podhorez, Midland, MI (US); Gary A. Roth, Home, MI (US); David C. Molzahn, Midland, MI (US); Timothy Adaway, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 15 days.

(21) Appl. No.: 11/982,604

(22) Filed: Nov. 2, 2007

(65) Prior Publication Data

US 2008/0108800 A1 May 8, 2008

Related U.S. Application Data

(60) Provisional application No. 60/856,739, filed on Nov. 3, 2006.

(51) Int. Cl.
*C07H 17/00* (2006.01)

(52) U.S. Cl. ........................ 536/7.1; 536/16.8; 536/18.5

(58) Field of Classification Search .................. 536/7.1, 536/16.8
See application file for complete search history.

(56) References Cited

U.S. PATENT DOCUMENTS 6,001,981 A * 12/1999 DeAmicis et al. ............ 536/7.1

* cited by examiner

*Primary Examiner*—Elli Peselev
(74) *Attorney, Agent, or Firm*—Carl D. Corvin

(57) ABSTRACT

Spinetoram is selectively produced in excellent yields by hydrogenating a mixture of 3'-O-ethyl spinosyn J and 3'-O-ethyl spinosyn L in a water miscible organic solvent using hydrogen gas and a heterogeneous catalyst.

3 Claims, No Drawings

SELECTIVE REDUCTION OF SPINOSYN FACTORS ET-J AND ET-L TO SPINETORAM

CROSS REFERENCE TO RELATED APPLICATIONS

This application claims priority to U.S. Ser. No. 60/856,739, filed Nov. 3, 2006, the disclosure of which is incorporated by reference in its entirety.

SUMMARY OF THE INVENTION

The present invention provides a selective catalytic reduction process for producing the insecticide spinetoram (also known as DE-175).

More specifically, the invention provides a process for producing spinetoram which comprises hydrogenating a mixture comprising about 50-90% by weight of 3'-O-ethyl spinosyn J and about 50-10% by weight of 3'-O-ethyl spinosyn L, in a water miscible organic solvent, with hydrogen gas at a pressure between 2 and 100 psi, in the presence of a heterogeneous catalyst capable of selectively reducing the 5,6-double bond of 3'-O-ethyl spinosyn J, until the 3'-O-ethyl spinosyn J is converted to 3'-O-ethyl-5,6-dihydro-spinosyn J.

The overall process is shown in SCHEME 1:

Spinetoram is the common name for a mixture of 50-90% (2R,3aR,5aR,5bS,9S,13S,14R,16aS,16bR)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7,15-dione (referred to in Scheme 1 as "dihydro-Et-J"), and 50-10% (2R,3aR,5aS,5bS,9S,13S,14R,16aS,16bS)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione (referred to in Scheme 1 as "Et-L").

DETAILED DESCRIPTION OF THE INVENTION

The invention utilizes a heterogeneous catalyst to give selective catalytic reduction of the 5,6 isolated double bond without concomitant reduction of the 13,14 conjugated double bond of Spinosyn factor Et-J. Factor Et-L is intentionally not reduced (beyond very small amounts) and is carried over to the product. Spinetoram is produced selectively and with excellent yields. Use of a heterogeneous catalyst as opposed to a homogeneous catalyst simplifies workup conditions.

The starting material for the hydrogenation is a mixture of the Spinosyn factors Et-J and Et-L obtained by alkylating a mixture of fermentation factors J and L. Procedures and strains for obtaining mixtures of spinosyns J and L are disclosed in U.S. Pat. No. 5,202,242. The alkylation procedure is described in U.S. Pat. No. 6,001,981. The disclosures of all US patents referred to herein are hereby incorporated by reference.

The mixture of Et-J and Et-L (Et-J/L) obtained from the alkylation can be used as a solid, obtained following workup and isolation of the alkylation step. Alternatively, Et-J/L can be used as a solution obtained after solvent exchange. The concentration of Et-J/L in solution can be anywhere from 5% to 50% wt., and preferably is used in the 20%-30% wt range. The weight percentages of Et-J and Et-L in the Et-J/L mixture are not critical provided they are selected to produce a product containing dihydro-Et-J and Et-L in a weight ratio of from 1/1 to 9/1.

The solvent used for the hydrogenation can be any typical organic solvent which is compatible with the hydrogenation conditions, such as toluene, ethyl acetate, alcohols (methanol, ethanol, 2-propanol), ethers (t-butylmethylether, tetrahydrofuran), and glycol ethers. More specifically, a water miscible solvent is desired to aid in spinetoram precipitation at the conclusion of the hydrogenation, with dimethoxyethane and 2-propanol preferred. Water can be used as a co-solvent from 0 to 25% wt., preferably in the 5%-10% wt range (based upon the main solvent). The presence of water increases the rate of hydrogenation and improves the catalyst filtration at the conclusion of the hydrogenation.

The hydrogenation can be carried out under a hydrogen atmosphere between 2 and 3000 psig pressure. Typically, the hydrogenation is conducted at 5-15 psig hydrogen. The yield and purity improve as reaction pressure is decreased, but the reaction rate decreases.

The temperature of the reaction mixture during hydrogenation can be from 0° C. up to the boiling point of the solvent being used. Typically the temperature will be in the range 0° C. to 100° C., more typically in the range 0° C. to 50° C. Most commonly the reaction is run at ambient temperature.

The catalyst used for the hydrogenation can be any heterogeneous catalyst found in the literature which is capable of reducing a double bond, for example palladium, platinum, rhodium, and nickel. These catalysts are generally used on an inert support such as carbon, $Al_2O_3$, $BaSO_4$, and $CaCO_3$, typically 0.5% to 10% wt catalyst to support. The catalysts can be dry or contain up to 60% wt water. The amount of catalyst used for the hydrogenation can be from 0.1 mole % to 10 mole % based upon the amount of starting factors Et-J/L, and most commonly is used from 1-3 mole %. Most important is the ability to selectively reduce the 5,6-double bond of Et-J without concomitant reduction of the 13,14-conjugated double bond of factors Et-J. 5% $Rh/Al_2O_3$, 5% Rh/C, 5% Pd/C, 5% $Pd/Al_2O_3$, for example, give excellent results. 1%-5% Pd/C have been successfully used. $Pd/CaCO_3$ has been successfully used. A mixed metal catalyst, e.g. Rh+Pd/C, can also be used.

Reaction selectivity increases as the catalyst charge is increased. A set of experiments gave the following results between mole % catalyst and amount of reduction at the 13,14 double bond: (1.2 mole % Pd/24+ hr reaction/2.3% over reduction), (1.9 mole % Pd/4 hr reaction/1.5% over reduction), and (4.2 mole % Pd/2 hr reaction/0.5% over reduction).

Pre-treatment of the feed solution with activated carbon reduces the amount of catalyst poisoning, and decreases the amount of catalyst necessary to obtain a reasonable reaction rate.

The pH of the feed solution should be below 7 to obtain good selectivity.

The workup and isolation of the hydrogenation reaction involves catalyst filtration through an inert filtering aid such as Celite or cellulose, followed by addition of water to precipitate the final product spinetoram. This present procedure avoids the tedious and time consuming workup necessary when using Wilkinson's catalyst, thus avoiding several problematic extractions and use of ether. Final product spinetoram is filtered from the aqueous/organic solvent and dried to provide spinetoram suitable for formulation.

EXAMPLE 1

Rhodium Hydrogenation of Solid Et-J/L to Spinetoram Using DME

A 2 L thick-walled Parr bottle was charged with 135 g (≈0.18 mole, ppt from $EtOH/H_2O$) of solid Et-J/L followed by 300 mL of 1,2-dimethoxyethane (DME). To the solution was added 9.3 g of 5% $Rh/Al_2O_3$ (4.5 mmol) and magnetic stirring was commenced. The bottle was connected to a hydrogenation setup, and pressured up to 6 psi with $N_2$. The pressure was relieved, and this procedure repeated four times. Finally, the bottle was pressured to 15 psi with $H_2$, relieved, and repressured to 15 psi with $H_2$. The black mixture was allowed to stir at 15 psi $H_2$ for 17 h, when $^1H$ NMR analysis indicated little reduction. The reaction mixture was inerted and relieved five times by pressuring up to 6 psi with $N_2$. The dark mixture was filtered through Celite to remove catalyst. The yellow solution was re-subjected to hydrogenation (40 psi $H_2$) with fresh 5% $Rh/Al_2O_3$ (9.3 g, 4.5 mmol). After 27 h $^1H$ NMR analysis indicate complete reduction of Et-J to dihydro-Et-J. The dark mixture was filtered through Celite and concentrated in vacuo to give 262 g of a thick dark oil. This was added dropwise over 1.50 h to 550 mL of water which had been pre-seeded with a sample of spinetoram. The temperature during the addition was kept <10° C. with icebath cooling. The thick, creamy gray mixture was allowed to stir at RT for 2 days, filtered, and washed twice with water. The paste like material was air dried in a hood overnight followed by vacuum oven drying at 45° C. to give 125 g of a light gray powder, mp 125°-130° C.

EXAMPLE 2

Rhodium Hydrogenation of Et-J/L Solution to Spinetoram Using IPA

A 2 L thick-walled Parr bottle was charged with 276 g (0.1 mole, 27.0% wt in iPrOH (IPA), Pilot Plant Batch 3) of Et-J/L followed by 10.0 g of water (5% wt of IPA). To the solution was added 2.57 g of 5% $Rh/Al_2O_3$ (1.25 mmol,) and magnetic stirring was commenced. The bottle was connected to a hydrogenation setup, and pressured up to 6 psi with $N_2$. The pressure was relieved, and this procedure repeated four times. Finally, the bottle was pressured to 15 psi with $H_2$, relieved, and repressured to 15 psi with $H_2$. The black mixture was allowed to stir at 15 psi $H_2$, and the reaction could be monitored via LC analysis (ACE-Ph column, 40° C., 55:45 $CH_3CN$/0.5% wt ammonium formate), watching for disappearance of Et-J and appearance of dihydro-Et-J. After 16 hrs, LC analysis (UV detection, 254 nm) indicated no remaining Et-J and 70.9 area % dihydro-Et-J. The reaction mixture was inerted and relieved five times by pressuring up to 6 psi with $N_2$. The dark mixture was filtered through a medium frit sintered glass funnel which had been pre-loaded with 5.1 g of cellulose. The filtration was slow, and took 10 min to complete. The filter was rinsed 2× with 10 mL of IPA. The dark solution was transferred to a 2 L vessel, and 402 g (2×wt IPA) of water was added dropwise over 4 h between 54°-57° C. with stirring. The cloudy, two phase, oily mixture was allowed to slowly cool to 25° C. over 12 h, and stirred here 30 h. Some gummy, dark material had formed on the sides of the reactor, and was knocked off into the stirred mixture. The solids were filtered to give a dark sugar-like sticky solid. The solids were washed once with 2:1 water/IPA, twice with water, and aspirator dried for 0.5 h to give 94.2 g of a hard, tacky solid. The solids were allowed to air dry in a hood two days to give 77.0 g of solid, and further dried in a vacuum oven at 40° C. gave 76.7 g of a light gray powder, mp 128°-132° C., 23% loss on drying. LC analysis using hexanophenone as an internal standard indicated 91.0% wt spinetoram, for an overall yield of 93% from Et-J/L.

EXAMPLE 3

Palladium Hydrogenation of Et-J/L Solution to Spinetoram Using IPA

A 2 L thick-walled Parr bottle was charged with 281 g (0.1 mole, 26.5% wt in i-PrOH (IPA)) of Et-J/L followed by 10.3 g of water (5% wt of IPA). To the solution was added 8.84 g of Pd/C (1.85 mmol, 53.8% wt $H_2O$) and magnetic stirring was commenced. The bottle was connected to a hydrogenation setup, and pressured up to 6 psi with $N_2$. The pressure was relieved, and this procedure repeated four times. Finally, the bottle was pressured to 15 psi with $H_2$, relieved, and re-pressured to 15 psi with $H_2$. The black mixture was allowed to stir at 15 psi $H_2$, and the reaction could be monitored via LC analysis (ACE-Ph column, 40° C., 55:45 $CH_3CN$/0.5% wt ammonium formate), watching for disappearance of Et-J and appearance of dihydro-Et-J. After 38 hrs, LC analysis (UV detection, 254 nm) indicated 2.0 area % Et-J and 62.9 area % dihydro-Et-J. LC analysis using ELSD indicated 0.7 area % Et-J, 70.6 area % dihydro-Et-J, and 1.9 area % tetrahydro-Et-J. The reaction mixture was inerted and relieved five times by pressuring up to 6 psi with $N_2$. The dark mixture was filtered through a medium frit sintered glass funnel which had been pre-loaded with 15 g of cellulose. The filtration was very slow, and took 25 min to complete. Dark fines had collected on the surface of the frit. The filter was rinsed 2× with 10 mL of IPA. The yellow solution was transferred to a 2 L vessel, and 410 g (2×wt IPA) of water was added dropwise over 4 h at 25° C. with stirring. White solids formed after 300 mL of the water had been added. The mixture was stirred at 25° C. for 20 h (later experiments indicated this length of digestion was not necessary, and the time was shortened to 4 h). The solids were filtered and washed 2× with 2:1 water/IPA and aspirator dried for 0.5 h to give 84.7 g of a white solid. The solids were allowed to air dry in a hood overnight to give 62.3 g of white solid. Final drying in a vacuum oven at 40° C. gave 60.4 g of a white, powdery solid, 28.7% loss on drying. LC analysis using diethyl phthalate as an internal standard indicated 90.9% wt spinetoram, for an overall yield of 73% from Et-J/L.

The invention claimed is:

1. A process for producing spinetoram which comprises: hydrogenating a mixture comprising about 50-90% by weight of 3'-O-ethyl spinosyn J and about 50-10% by weight of 3'-O-ethyl spinosyn L, in a water miscible organic solvent, with hydrogen gas at a pressure between 2 and 3000 psig, in the presence of a heterogeneous catalyst capable of selectively reducing the 5,6-double bond of 3'-O-ethyl spinosyn J, until the 3'-O-ethyl spinosyn J is converted to 3'-O-ethyl-5,6-dihydrospinosyn J.

2. A process of claim 1 wherein the solvent is isopropyl alcohol.

3. A process of claim 1 wherein the heterologous catalyst is 5% $Rh/Al_2O_3$ or 5% Pd/C.

* * * * *